United States Patent [19]

Kubo et al.

[11] Patent Number: 5,099,065

[45] Date of Patent: Mar. 24, 1992

[54] BETAINE COMPOUND AND DETERGENT COMPOSITION

[75] Inventors: Makoto Kubo; Kohshiro Sotoya, both of Wakayama; Takashi Matsuo, Saitama; Kazuyuki Yahagi, Tokyo, all of Japan

[73] Assignee: Kao Corporation, Tokyo, Japan

[21] Appl. No.: 658,292

[22] Filed: Feb. 20, 1991

[30] Foreign Application Priority Data

Feb. 27, 1990 [JP] Japan .................................. 2-46821
Mar. 6, 1990 [JP] Japan .................................. 2-56140
Jul. 9, 1990 [JP] Japan .................................. 2-181115

[51] Int. Cl.$^5$ ........................................... C07C 229/00
[52] U.S. Cl. ................................. 562/564; 562/104; 562/107; 562/561; 252/547
[58] Field of Search ............................. 562/561, 564

[56] References Cited

U.S. PATENT DOCUMENTS 4,090,969 5/1978 Koch .................................. 562/564
4,124,632 11/1978 Kalopissis ........................ 562/564
4,374,056 2/1983 Watanabe ......................... 562/564

FOREIGN PATENT DOCUMENTS 64-19051 1/1989 Japan .................................. 562/564

Primary Examiner—Michael L. Shippen
Attorney, Agent, or Firm—Birch, Stewart, Kolasch & Birch

[57] ABSTRACT

The present invention provides a novel betaine compound represented by the general formula:

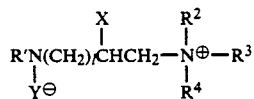

wherein $R^1$ is a straight-chain or branched alkyl, alkenyl or hydroxyalkyl group having 8 to 22 carbon atoms; X is H or a hydroxy group; $R^2$, $R^3$ and $R^4$ each represent an alkyl group having 1 to 4 carbon atoms; Y is $-CH_2CH(OH)CH_2SO_3$, $-(CH_2)_nSO_3$ or $-(CH_2)_mCO_2$; n is 2 to 5; m is 1 to 5; and l is 0 to 5; a process for the preparation of the same; and a detergent composition containing the same. This detergent composition exhibits excellent foaming power and detergency and is lowly irritant, thus being suitable for a base of a body or hair shampoo.

1 Claim, No Drawings

BETAINE COMPOUND AND DETERGENT COMPOSITION

BACKGROUND OF THE INVENTION

1. Field of the Invention

The present invention relates to a novel betaine compound and a process for the preparation thereof. More particularly, it relates to a betaine compound which acts on the skin mildly and exhibits excellent foaming power and detergency and which is useful as a surfactant for a hair or body detergent composition, and a process for the preparation thereof.

2. Description of the Prior Art

Recently, a surfactant for a detergent has been required to exhibit not only excellent surface activity but also other excellent characteristics such as biodegradability and safety and low irritation to the eye and skin. Therefore, acylated amino acid or imidazoline type of surfactants have been widely used as those satisfying this requirement.

However, these surfactants are generally poor in foaming power and detergency which are essential to surface activity and therefore generally used as a component of a shampoo or the like, not alone, but rather together with an anionic surfactant such as an alkyl ether sulfate or alkyl sulfate, though they are excellent in safety.

However, the simultaneous use of such an anionic surfactant is in danger of roughening the skin, because the surfactant is highly irritating to the skin.

Accordingly, the development of a surfactant which is excellent in foaming power and detergency and highly safe has been strongly desired.

SUMMARY OF THE INVENTION

Under these circumstances, the present inventors have intensively studied to obtain a surfactant which is excellent enough to be used as a component in a hair or body detergent composition with respect to foaming power, detergency and safety; and have found that a betaine compound represented by the following general formula:

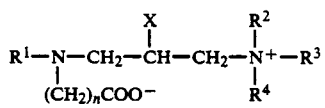

(1)

wherein $R^1$ represents a straight-chain or branched alkyl, alkenyl or hydroxyalkyl group having 8 to 22 carbon atoms; X represents H or a hydroxyl group; $R^2$, $R^3$ and $R^4$ each represent an alkyl group having 1 to 4 carbon atoms; and n represents a number of 1 to 5, is fit for the purpose of the present invention. The present invention has been accomplished on the basis of this finding.

Namely, the present invention provides a novel betaine compound represented by the general formula:

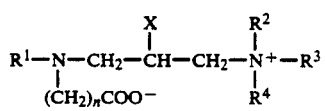

(1)

wherein $R^1$ represents a straight-chain or branched alkyl, alkenyl or hydroxyalkyl group having 8 to 22 carbon atoms; X represents H or a hydroxyl group; $R^2$, $R^3$ and $R^4$ each represent an alkyl group having 1 to 4 carbon atoms; and n represents a number of 1 to 5, a process for the preparation of the same; and a surfactant containing the same.

The present invention will now be described in more detail.

Since no reports have been found on the compounds represented by the above general formula (1) in literature and patents, they are novel compounds.

The betaine compound of the present invention can be prepared by the following two processes <1> and <2>:

Preparation process <1>

Amination

A compound represented by the general formula:

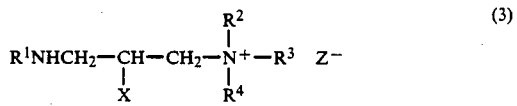

(3)

wherein $R^1$ represents a straight-chain or branched alkyl, hydroxyalkyl or alkenyl group having 8 to 22 carbon atoms; X represents H or a hydroxyl group; $R^2$, $R^3$ and $R^4$ each represent an alkyl group having 1 to 4 carbon atoms; and Z is OH, a halogen atom or an alkylsulfate having 1 to 4 carbon atoms, is prepared by reacting a primary aliphatic amine represented by the general formula: $R^1NH_2$ (wherein $R^1$ represents a straight-chain or branched alkyl, alkenyl or hydroxyalkyl group having 8 to 22 carbon atoms) with, 1 to 3 times by mole as much, a compound represented by the general formula:

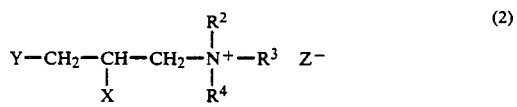

(2)

wherein Y represents a halogen atom; X represents H or a hydroxyl group; $R^2$, $R^3$ and $R^4$ each represent an alkyl group having 1 to 4 carbon atoms; and Z represents OH, a halogen atom or an alkylsulfate having 1 to 4 carbon atoms.

Conversion into betaine

A betaine compound (1) can be easily prepared by reacting the compound (3) with, 1 to 3 times by mole as much, a halogenated lower alkylenecarboxylic acid or an ester or metal salt thereof represented by the general formula:

$$Y(CH_2)_nCOOM \qquad (4)$$

wherein Y represents a halogen atom; n represents a number of 1 to 5; M represents H, a lower alkyl group or an alkali metal.

This preparation process can be represented by the following reaction scheme, more particularly:

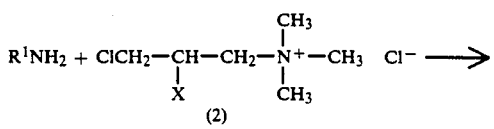

-continued

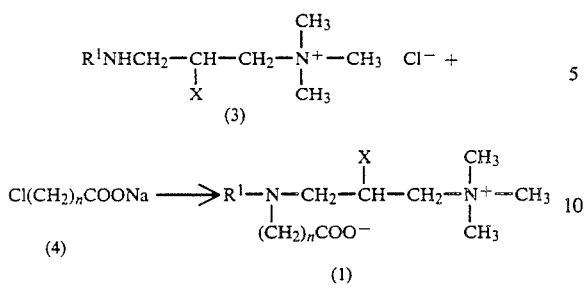

(1)

wherein R¹, X and n are each as defined above.

The reaction between the primary amine and the compound (2) is generally conducted by dropping the amine into an aqueous solution of the compound (2). After the completion of the dropping, it is preferable in order to make the reaction between the amine and the compound (2) proceed, that the obtained mixture be kept at a pH of 8 to 12, if necessary, by the addition of a solution of an alkali such as sodium hydroxide or potassium hydroxide. Although the pH of the reaction system is preferably 8 or above, a value thereof exceeding 12 is unfavorable because the compound (2) is hydrolyzed under such a condition. Although the above reaction proceeds even at an ordinary temperature, a higher reaction temperature can result in a higher reaction rate. However, the hydrolysis of the compound (2) is accelerated when the temperature or the pH is too high. Accordingly, the reaction temperature is limited to 100° C. or below, preferably 90° C. or below.

According to the preparation process <1>, the molar ratio of the compound (2) to the primary amine is generally between 1 : 1 and 3 : 1, preferably between 1.1:1 and 1.5:1. A lower molar ratio than the range will decrease conversion. A higher one will leave a large amount of the hydrolysate of the compound (2) to remain in the reaction mixture.

The completion of the reaction between the primary amine and the compound (2) can be ascertained by analyzing the reaction system for the residual amount of the amine by high-performance liquid chromatography. Accordingly, after the ascertainment of the completion of the reaction, an aqueous solution of a compound represented by the general formula (4) which has been preliminarily prepared is dropped into the obtained mixture to conduct the conversion into betaine. Thereafter, an aqueous solution of an alkali as described above is added to the mixture in such an amount so as to adjust the pH thereof from 8 to 12, preferably from 9 to 11, while the temperature of the mixture is kept in a range of 50° to 100° C., preferably 70° to 90° C. If the temperature is lower than 50° C., the reaction will proceed too slowly, while if it exceeds 100° C., the hydrolysis of the compound represented by the general formula (4) will be accelerated.

According to the preparation process <1>, the molar ratio of the halogenated lower alkylenecarboxylic acid or ester or alkali metal salt thereof (4) to the betaine precursor (3) is generally between 1 : 1 and 3 : 1, preferably between 1.1 : 1 and 1.5 : 1.

According to the preparation process <1>, the reaction between the primary amine and the compound (2) generally takes 1 to 12 hours, though the reaction time varies depending upon the reaction temperature and the pH of the reaction system. Further, the conversion step generally takes 1 to 12 hours, though the reaction time also varies depending upon the reaction temperature and the pH of the reaction system.

The reaction medium may be either water or a mixture thereof with a lower alcohol such as ethanol or isopropyl alcohol or a diol such as 1,3-propanediol or propylene glycol.

Preparation process <2>

Amination

A compound represented by the general formula:

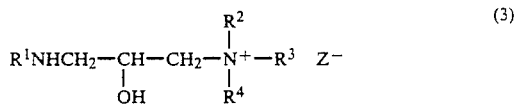

wherein R¹ represents a straight-chain or branched alkyl, hydroxyalkyl or alkenyl group having 8 to 22 carbon atoms; R², R³ and R⁴ each represent an alkyl group having 1 to 4 carbon atoms; and Z represents OH, a halogen atom or an alkylsulfate having 1 to 4 carbon atoms, is prepared by reacting a primary amine as described in the foregoing preparation process <1> with a glycidyltrialkylammonium salt represented by the general formula;

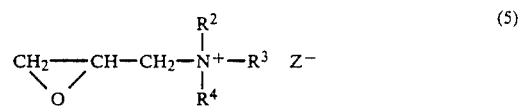

², R³ and R⁴ each represent an alkyl group having 1 to 4 carbon atoms; and Z represents OH, a halogen atom or an alkylsulfate having 1 to 4 carbon atoms.

then the obtained compound (3) is converted into an objective betaine compound (1) under the same conditions as those employed in Preparation process <1>.

This preparation process can be represented by the following reaction scheme, more particularly:

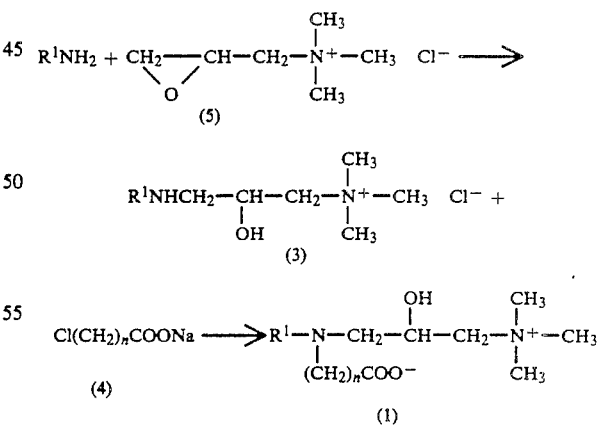

(1)

wherein R¹ and n are each as defined above.

In the reaction between the glycidyltrialkylammonium salt represented by the general formula (5) and the primary amine, the molar ratio of the former to the latter is between 1:1 and 3:1. A lower ratio than the range will decrease the conversion. A higher one will leave a large amount of the hydrolysate of the compound (5) to remain in the reaction mixture unfavorably. Further, the reaction temperature is 50° to 120° C., preferably 60° to 100° C. If the reaction temperature is below this range, the reaction will be too slow, while if it is above this range, coloration will occur unfavorably.

In order to secure the reactivity between the amine and the glycidyltrialkylammonium salt (5) to make the reaction between them proceed at an acceptable rate, it is preferable to keep the pH of the reaction system in a range of 8 to 12 by the addition of a proper amount of an aqueous solution of an alkali. If the pH is below this range, the reaction will be too slow, while if it is above this range, a by-product will generate to lower the yield.

The conversion into betaine in Preparative process <2> may be conducted under the same conditions as those described in Preparation process <1>.

Although all of the reactions described in Preparation processes <1> and <2> may be conducted either in the air or in an atmosphere of an inert gas, it is preferable with respect to the prevention of coloration that they be conducted in an atmosphere of an inert gas.

The primary amine $R^1NH_2$ (wherein $R^1$ is as defined above) to be used in the present invention includes octylamine, decylamine, dodecylamine, tetradecylamine, hexadecylamine, octadecylamine, oleylamine, behenylamine isostearylamine and cocoylamine.

Further a compound represented by the general formula (1) wherein n is 2, which corresponds to a compound represented by the general formula (1') or (1''), can be prepared also by the following process <3>:

Preparation process <3>

A betaine compound represented by the general formula:

$$R^1-N-CH_2-\underset{X}{\overset{|}{C}}H-CH_2-\underset{R^4}{\overset{R^2}{\overset{|}{N^+}}}-R^3 \quad (1')$$
$$|$$
$$CH_2CH_2COO^-$$

wherein $R^1$ represents a straight-chain or branched alkyl, alkenyl or hydroxyalkyl group having 8 to 22 carbon atoms; X represents H or a hydroxyl group; and $R^2$, $R^3$ and $R^4$ each represent an alkyl group having 1 to 4 carbon atoms, or the general formula:

$$R^1-N-CH_2-\underset{OH}{\overset{|}{C}}H-CH_2-\underset{R^4}{\overset{R^2}{\overset{|}{N^+}}}-R^3 \quad (1'')$$
$$|$$
$$CH_2CH_2COO^-$$

wherein $R^1$, $R^2$, $R^3$ and $R^4$ are each as defined above, can be prepared by reacting a primary amine as described above with acrylonitrile to form a compound represented by the general formula:

$$R^1NHCH_2CH_2C\equiv N \quad (6)$$

wherein $R^1$ represents a straight-chain or branched alkyl, alkenyl or hydroxyalkyl group having 8 to 22 carbon atoms, (cyanoethylation), and converting the obtained compound (6) into an objective betaine compound through one of the four routes which will be described below.

This preparation process will now be described in more detail.

Cyanoethylation

A primary aliphatic amine represented by the formula : $R^1NH_2$ (wherein $R^1$ represents a straight-chain or branched alkyl, alkenyl or hydroxyalkyl group having 8 to 22 carbon atoms) is reacted with 0.98 to 1.05 times by mole as much acrylonitrile at a temperature of 30° to 80° C. in the presence of water or a polar solvent such as ethanol or isopropyl alcohol to form a compound represented by the general formula:

$$R^1NHCH_2CH_2C\equiv N \quad (6)$$

wherein $R^1$ is as defined above. Then, the compound (6) is converted into a compound having the formula (1') or (1'') through one of the following four routes:

Route 1

A betaine compound (1') can be easily prepared by reacting the compound (6) with 1 to 3 times by mole as much a compound represented by the general formula:

$$Y-CH_2-\underset{X}{\overset{|}{C}}H-CH_2-\underset{R^4}{\overset{R^2}{\overset{|}{N^+}}}-R^3 \quad Z^- \quad (2)$$

wherein $R^2$, $R^3$, $R^4$ X, Y and Z are each as defined above,
in the presence of a dehydrohalogenating agent to form a compound represented by the general formula:

$$R^1NCH_2\underset{CH_2CH_2C\equiv N}{\overset{X}{\overset{|}{C}}HCH_2}-\underset{R^4}{\overset{R^2}{\overset{|}{N^+}}}-R^3 \quad Z^- \quad (7)$$

wherein $R^1$, $R^2$, $R^3$, $R^4$, X and Z are each as defined above,
and hydrolyzing this compound (7) in the presence of a basic compound.

Route 2

A betaine compound (1'') can be easily prepared by reacting the compound (6) with 0.98 to 1.05 times by mole as much an epihalohydrin represented by the general formula:

$$\underset{O}{\overset{CH_2CHCH_2Y}{\diagdown \diagup}} \quad (9)$$

wherein Y is as defined above, at a temperature of 30° to 80° C. to form a compound represented by the general formula:

$$R^1N-CH_2-\underset{OH}{\overset{|}{C}}H-CH_2Y \quad (12)$$
$$|$$
$$CH_2CH_2C\equiv N$$

wherein $R^1$ and Y are each as defined above, reacting the compound (12) with 1 to 5 times by mole as much a trialkylamine represented by the general formula:

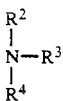
(11)

wherein $R^2$, $R^3$ and $R^4$ are each as defined above, at a temperature of 80° to 130° C., and hydrolyzing the obtained product in the presence of a basic compound.

Route 3

A betaine compound (1″) can be easily prepared by hydrolyzing the compound (6) in the presence of a basic compound to form a compound represented by the general formula:

$$R^1NHCH_2CH_2COOM \quad (8)$$

wherein $R^1$ and M are each as defined above, reacting the compound (8) with 0.98 to 1.05 times by mole as much an epihalohydrin represented by the general formula:

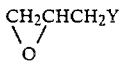
(9)

wherein Y is as defined above, at a temperature of 30° to 80° C. to form a compound represented by the general formula:

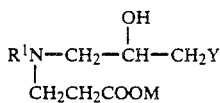
(10)

wherein $R^1$, Y and M are each as defined above, and reacting the compound (10) with 1 to 5 times by mole as much a trialkylamine (11) as defined above at a temperature of 80° to 130° C.

Route 4

A betaine compound (1′) can be easily prepared by hydrolyzing the compound (6) in the presence of a basic compound to form a compound represented by the general formula:

$$R^1NHCH_2CH_2COOM \quad (8)$$

wherein $R^1$ and M are each as defined above, and reacting the compound (8) with 1 to 3 times by mole as much a compound represented by the general formula:

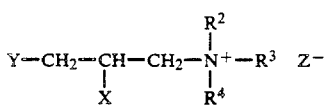
(2)

wherein $R^2$, $R^3$, $R^4$, X, Y and Z are each as defined above, in the presence of a dehydrohalogenating agent.

The betaine compound represented by the general formula (1) prepared by the process according to the present invention exhibits surface activity and a surfactant containing the same as a main component exhibits excellent foaming power and detergency and is low in irritancy, so that it is usable as a base in not only a hair detergent composition but also a body detergent composition.

The present invention also relates to another novel betaine compound (21) and a process for the preparation thereof.

Namely, the present invention provides a novel betaine compound represented by the general formula:

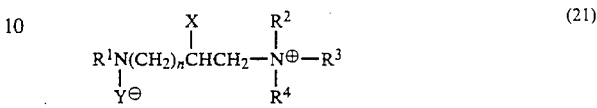
(21)

wherein $R^1$ represents a straight-chain or branched alkyl, alkenyl or hydroxyalkyl group having 8 to 22 carbon atoms; X represents H or a hydroxyl group; $R^2$, $R^3$ and $R^4$ each represent an alkyl group having 1 to 4 carbon atoms: Y represents —CH$_2$CH(OH)CH$_2$SO$_3$ or —(CH$_2$)$_{2\sim5}$SO$_3$; and n represents 0 or an integer of 1 to 5, with the proviso that X is H or a hydroxyl group when n is 1, while X is H when n is 0, 2 or 3, a process for the preparation of the same, and a surfactant containing the same.

The present invention will now be described in more detail.

Since no reports have been found on the compounds represented by the general formula (21) in literature and patents, these compounds are novel.

The betaine compound represented by the general (21) can be prepared by either of the following two processes <21> and <22>:

Preparation process <21>

Amination

A compound represented by the general formula:

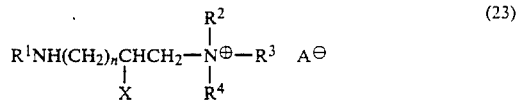
(23)

wherein $R^1$ represents a straight-chain or branched alkyl, alkenyl or hydroxyalkyl group having 8 to 22 carbon atoms; X represents H or a hydroxyl group; $R^2$, $R^3$ and $R^4$ each represent an alkyl group having 1 to 4 carbon atoms; A is OH, a halogen atom or an alkylsulfate having 1 to 4 carbon atoms; and n is as defined above, is prepared by reacting a corresponding primary amine with 1 to 3 times by mole as much a compound represented by the general formula:

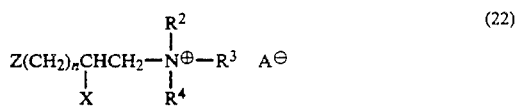
(22)

wherein Z represents a halogen atom; X represents H or a hydroxyl group; $R^2$, $R^3$ and $R^4$ each represent an alkyl group having 1 to 4 carbon atoms; A represents OH, a halogen atom or an alkylsulfate having 1 to 4 carbon atoms and n is defined above.

Conversion into betaine

A betaine compound (21) can be prepared by reacting the compound (23) with 1 to 3 times by mole as much a metal salt of 3-halo-2-hydroxypropylenesulfonic acid represented by the general formula:

$$ZCH_2CH(OH)CH_2SO_3M \quad (24)$$

wherein Z represents a halogen atom and M represents an alkali metal,
or by reacting the compound (23) with 1 to 3 times by mole as much a compound represented by the general:

$$Z(CH_2)_{2\sim 5}SO_3M \quad (25)$$

wherein Z and M are each as defined above.

This preparation process can be represented by the following reaction scheme more particularly:

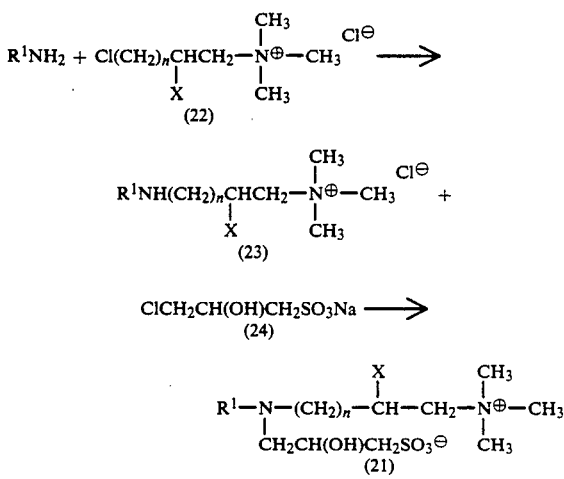

wherein $R^1$, X and n are each as defined above.

The reaction between the primary amine and the compound (22) is generally conducted by dropping the amine into an aqueous solution of the compound (22). After the completion of the dropping, it is preferable, in order to make the reaction between the amine and the compound (22) proceed, that the obtained mixture be kept at a pH of 8 to 12, if necessary, by the addition of a solution of an alkali such as sodium hydroxide or potassium hydroxide. Although the pH of the reaction system is preferably 8 or above, a value thereof exceeding 12 is unfavorable because the compound (22) is hydrolyzed under such a condition. Although the above reaction proceeds even at an ordinary temperature, a higher reaction temperature can give a higher reaction rate. However, the hydrolysis of the compound (22) is accelerated when the temperature or the pH is too high. Accordingly, the reaction temperature is limited to 100° C. or below, preferably 90° C. or below.

According to the preparation process <21>, the molar ratio of the compound (22) to the primary amine is generally between 1 : 1 and 3 : 1, preferably between 1.1 : 1 and 1.5 : 1. If the molar ratio is below this range, the conversion will be low, while if it is above this range, a large amount of the compound (22) or hydrolyzate thereof will remain in the reaction between the primary amine and the compound (22) can be ascertained by analyzing the reaction system for the residual amount of the amine by high-performance liquid chromatography. Accordingly, after the ascertainment of the completion of the reaction, an aqueous solution of a compound represented by the general formula (24) or (25) which has been preliminarily prepared is dropped into the obtained mixture to conduct the conversion into betaine. Thereafter, an aqueous solution of an alkali as described above is added to the mixture so as to adjust the pH thereof to from 8 to 12, preferably from 9 to 11, while the temperature of the mixture is kept in a range of 50° to 100° C., preferably 70° to 90° C. If the temperature is lower than 50° C., the reaction will proceed too slowly, while if it exceeds 100° C., the hydrolysis of the compound (24) or (25) will be accelerated.

According to the preparation process <21>, the molar ratio of the compound represented by the general formula (24) or (25) to the betaine precursor (23) is generally between 1 : 1 and 1 : 3, preferably between 1.1 : 1 and 1.5 : 1. If the molar ratio is below this range, the conversion will be low, while if it is above this range, a large amount of the compound (24) or (25) or hydrolyzate thereof will remain in the reaction mixture unfavorably.

According to the preparation process <21>, the amination generally takes 1 to 12 hours, though the reaction time of the amination varies depending upon the temperature and the pH of the reaction system. Further the subsequent reaction also generally takes 1 to 12 hours, though the reaction time varies depending upon the temperature and the pH of the reaction system.

The reaction medium may be either water or a mixture thereof with a lower alcohol such as ethanol or isopropyl alcohol or a diol such as 1,3-propanediol or propylene glycol.

Preparation process <22>

Amination

A compound represented by the general formula:

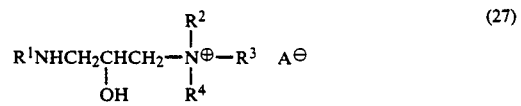

wherein $R^1$ represents a straight-chain or branched alkyl, alkenyl or hydroxyalkyl group having 8 to 22 carbon atoms; $R^2$, $R^3$ and $R^4$ each represent an alkyl group having 1 to 4 carbon atoms; and A represents OH, a halogen atom or an alkylsulfate, is prepared by treating a corresponding primary amine with a glycidylalkylammonium salt represented by the general formula:

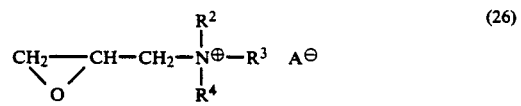

wherein $R^2$, $R^3$ and $R^4$ each represent an alkyl group having 1 to 4 carbon atoms; and A is OH, a halogen atom or an alkylsulfate having 1 to 4 carbon atoms.

Then, the obtained compound (27) is converted into an objective betaine compound (21) under the same conditions as those described in the preparation process <21>.

This preparation process can be represented by the following reaction scheme more particularly:

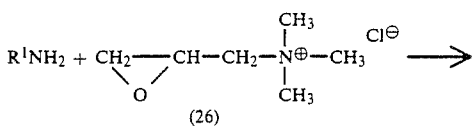

(26)

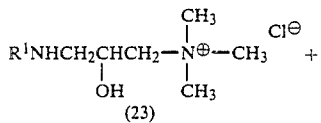

(23)

ClCH₂CH(OH)CH₂SO₃M ⟶
(24)

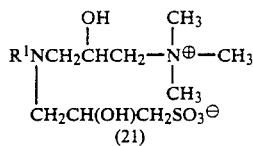

(21)

wherein R¹ and M are each as defined above.

In the reaction between a glycidyltrialkylammonium salt represented by the general formula (26) and the primary amine, the molar ratio of the compound of the general formula (26) to the amine is between 1 : 1 and 3 : 1. If the molar ratio is below this range, the conversion will be low, while if it is above this range, a large amount of the compound (26) or hydrolyzate thereof will remain in the reaction mixture unfavorably. The reaction temperature is 30° to 120° C., preferably 50° to 90° C. If the reaction temperature is below this range, the reaction rate will be low, while if it is above this range, coloration will occur unfavorably. In order to secure the reactivity between the primary amine and the glycidyltrialkylammonium salt (26) to make the reaction between them proceed at an acceptable rate, it is preferable to keep the pH of the reaction system in a range of 8 to 12 by the addition of a proper amount of an aqueous solution of an alkali. If the pH is below this range, the reaction rate will be low, while if it is above this range, a large amount of a by-product will generate to lower the yield.

The conversion step in Preparation process <22> may be conducted under the same conditions as those described in Preparation process <21>.

Although all of the reactions may be conducted in the air or in an atmosphere of an inert gas, it is preferable in respect of the prevention of coloration that they be conducted in an atmosphere of an inert gas.

The primary amine R¹NH₂ (wherein R¹ is as defined above) to be used in the present invention includes octylamine, decylamine, dodecylamine, tetradecylamine, hexadecylamine, octadecylamine, oleylamine, behenylamine isostearylamine and cocoylamine.

The betaine compound represented by the general formula (21) according to the present invention exhibits surface activity and a surfactant containing the same as a main component exhibits excellent foaming power and detergency and is low in irritancy, so that it is usable as a base for not only a hair detergent composition but also a body detergent composition.

Further, the present invention also relates to a detergent composition which is low in irritancy to the skin and hair and exhibits a detergency and a foaming power suitable for body shampoos, hair shampoos and so on.

The inventors of the present invention have found that a detergent composition containing a specific betaine compound (31) as an active ingredient is low in irritancy to the skin and hair, exhibits high foaming power and detergency and is excellent in the stability in hard water to accomplish the present invention.

Namely, the present invention provides a detergent composition containing a betaine compound represented by the general formula:

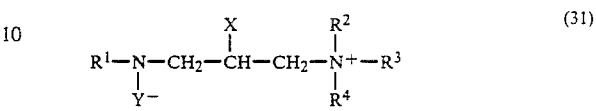

wherein R¹ represents a straight-chain or branched alkyl, alkenyl or hydroxyalkyl group having 8 to 22 carbon atoms; X represents H or a hydroxyl group; R², R³ and R⁴ are the same or different from each other and each represent an alkyl group having 1 to 4 carbon atoms; Y represents —CH₂CH(OH)CH₂SO₃, —(CH₂)ₙSO₃ or —(CH₂)ₘCO₂; n represents a number of 2 to 5; and m represents a number of 1 to 5, as an active ingredient.

The detergent composition of the present invention characterized by containing a betaine compound represented by the general formula (31) as a main active component is suitable as a hair or skin detergent composition as babies and children or for a shampoo for users who shampoo their hairs every day or who are unintentionally brought into contact with a shampoo at their work for long periods of time.

The content of the betaine compound represented by the general formula (31) in the detergent composition of the present invention is 0.1 to 50% by weight when the composition is liquid, 0.1 to 80% by weight when it is pastelike, and 50 to 99% by weight when it is solid or powdery.

Among betaine compounds represented by the general formula (31), those represented thereby wherein R¹ is a straight-chain or branched alkyl or alkenyl group having 12 to 18 carbon atoms are desirable. Further, compounds represented by the formula (31) wherein R¹ is a lauryl or myristyl group; all of R², R³ and R⁴ are CH₃; Y⁻ is —CH₂COO⁻ or —CH₂CH(OH)CH₂SO₃⁻; and X is a hydroxyl group are more desirable.

The detergent composition of the present invention may contain a conventional anionic, nonionic or amphoteric surfactant in addition to the betaine compound represented by the general formula (31) to improve the foaming power. The anionic surfactant includes alkyl sulfate salts, alkyl ether sulfate salts, alkyl phosphate salts and sulfosuccinate salts; and the amphoteric surfactant includes amidobetaine, alkyltaurine, carbobetaine and hydroxysulfobetaine. Particularly, a combination of the compound (31) with a saccharose nonionic surfactant such as alkyl polyglucoside is more effective in improving the foaming power.

Further the detergent composition of the present invention may contain various polymers, for example, water-soluble polymers such as cationized cellulose or water-dispersible silicon derivative as a conditioning component in addition to the betaine compound (31) and the above surfactants. Furthermore a cationic surfactant or a higher alcohol may be added to the detergent composition. If necessary, the detergent composition may contain various additives such as a perfume, a dyestuff, a preservative, an antioxidant, a thickening agent, an anti-dandruff agent, drugs (such as bactericide, antiphlogistic and vitamine) and additives described in the Encyclopedia of Shampoo Ingredients (Micelle press, 1985).

The detergent composition of the present excellent creamy foam and is a low irritant, so that it is suitable particularly as a body shampoo or a hair shampoo.

The effects of the detergent composition according to the present invention are exhibited, not only when tap water is used, but also when a water having a high hardness such as ground water, hot spring or sea water is used.

DESCRIPTION OF THE PREFERRED EMBODIMENTS

The present invention will now be described in more detail by referring to the following Examples, though the scope of the present invention is not limited by them.

With respect to betaine compound (1)

EXAMPLE 1

Amination [synthesis of compound (3)]

185 g of dodecylamine (MW: 185), 200 g of ion-exchanged water and 100 g of ethanol were fed into a 2-l four-necked flask equipped with a stirrer, a condenser, a thermometer and a dropping funnel. The obtained mixture was heated to 75° C. under stirring. While keeping the mixture at that temperature, a pH electrode was inserted into the mixture and a 40% aqueous solution of sodium hydroxide was dropped into the flask to adjust the pH of the mixture to 10.

489 g of a 50% aqueous solution of 3-chloro-2-hydroxypropyltrimethylammonium chloride (MW: 188) was dropped into the flask over a period of 2 hours, while keeping the pH of the mixture at 10 by the suitable dropwise addition of 40% sodium hydroxide. After the completion of the dropping of 3-chloro-2-hydroxypropyltrimethylammonium chloride, the heating and stirring of the mixture were continued with the pH thereof kept at 10, while analyzing the reaction system for the residual content of the dodecyl amine by high-performance liquid chromatography every hour.

After 6 hours from the completion of the dropping of 3-chloro-2-hydroxypropyltrimethylammonium chloride, the dodecylamine content of the reaction system lowered to 1%, and therefore the reaction mixture was transferred to the next step.

Conversion into betaine [synthesis of compound (1)]

The above reaction mixture was heated to 80° C. 379 g of a 40% aqueous solution of sodium monochloroacetate (MW: 116.5) which had been preliminarily prepared was dropped into the mixture over a period of 2 hours, while keeping the pH of the mixture at 10 by the suitable dropwise addition of a 40% aqueous solution of an alakli. While keeping the pH of the reaction system at 10 and heating and stirring the system, the reaction was conducted until the concentration of the compound (3) in the system, lowered to 1% as determined by high-performance liquid chromatography, and thereafter discontinued.

The obtained reaction mixture wa purified with an electrodialyzer. A part of the purified mixture was evaporated to dryness and subjected to IR spectroscopic analysis and mass spectrometric analysis to thereby ascertain that a compound represented by the general formula (1), i.e., N-dodecyl-N-(3trimethylammonio-2-hydroxypropyl)aminoacetate was formed. The obtained compound was examined for foaming power, detergency and irritativeness to the skin and the results are given in Table 1.

Results of IR spectroscopic analysis and mass spectrometric analysis

<IR spectroscopic analysis>

An intense absorption assignable to a carboxylate ion was observed at 1590 cm$^{-1}$ (6.25 $\mu$).

<mass spectrometric analysis> device:
  mfd. by JEOL, Ltd., SX-102 type
  mass spectrometric type
conditions of measurement:
  introduction: direct
  ionization: FAB (Fast Atom Bombardment)
results:
  fragment
  molecular weight of ion
  359
  300
  256

Three main peaks were observed, among which the peak of 359 is assignable to a parent ion (M+1). Thus the obtained compound was ascertained to have a betaine structure according to the present invention.

EXAMPLE 2

The same reaction procedure as that of Example 1 was repeated except that tetradecylamine was used as the starting amine. The obtained compound was examined for foaming power, detergency and irritativeness to the skin and the results are given in Table 1 together with those of Example 1.

Example 3

The same reaction procedure as that of Example 1 was repeated except that 3-chloropropyltrimethylammonium chloride was used as the raw material. The obtained compound was examined for foaming power, detergency and irritativeness to the skin and the results are given in Table 1 together with those of Example 1.

Results of IR spectroscopic analysis and mass spectrometric analysis

<IR spectroscopic analysis>

An intense absorption assignable to a carboxylate ion was observed at 1570 cm$^{-1}$ (6.45 $\mu$).

<mass spectrometic analysis>

This analysis was conducted under the same conditions as those of Example 1.

A peak of 343 assignable to a parent ion (M+1) was observed to identify the obtained compound as a betaine compound according to the present invention. Example 4 [synthesis of betaine compound (1'); route 1]

Cyanoethylation 185 g of dodecylamine (MW: 185) and 10 g of ethanol were fed into the same reactor as that used in Example 1. The obtained mixture was heated to 50° C. under stirring. 53 g of acrylonitrile (MW : 53) was dropped into the mixture over a period of one hour. The obtained mixture was aged for 2 hours and examined for dodecylamine concentration by gas chromatography. The concentration was 0.3%. Therefore the reaction mixture was transferred to the next step.

Quaternization

The above reaction mixture was heated to 80° C. and 200 g of ethanol, 50 g of ion-exchanged water and 489 g of a 50% aqueous solution of 3-chloro-2-hydroxypropyl-trimethylammonium chloride (MW: 188) were dropped thereinto over a period of 2 hours.

During the above dropping, 40% sodium hydroxide was suitably dropped into the mixture to thereby keep the pH thereof at 9. While keeping the pH of the mixture at 9 and heating and stirring the mixture, the reaction was conducted until the concentration of N-(2-cyanoethyl)-N-dodecylamine in the reaction system lowered to below 1% as determined by high-performance liquid chromatography.

Hydrolysis

After the temperature of the above reaction mixture had been lowered to 75° C., the pH thereof was adjusted to 11 by the suitable dropwise addition of 40% sodium hydroxide to conduct the reaction for 6 hours. Then the reaction was discontinued.

The obtained reaction mixture was purified by electrodialysis. A part of the purified mixture was evaporated to dryness and subjected to IR spectroscopic analysis and mass spectrometric analysis to thereby ascertain that a compound represented by the general formula (1'), i.e., N-dodecyl-N-(3-trimethylammonio-2-hydroxypropyl)aminopropionate was formed. The obtained compound was examined for foaming power, detergency and irritativeness to the skin and the results are given in Table 1.

Results of IR spectroscopic analysis and mass spectrometric analysis

<IR spectroscopic analysis>

An intense absorption assignable to a carboxylate ion was observed at 1560 cm$^{-1}$ (6.4 μ).

<mass spectroscopic analysis>
device:
 mfd. by JEOL, Ltd., SX-102 type
 mass spectrometric type
conditions of measurement:
 introduction: direct
 ionization: FAB (Fast Atom Bombardment)
results:
 fragment
 molecular weight of ion
 373
 314
 270

Three main peaks were observed, among which the peak of 373 is assignable to a parent ion (M+1). Thus the obtained compound was ascertained to have a structure according to the present invention. Example 5 [synthesis of betaine compound (1"); route 2]

Cyanoethylation

This step was conducted in a similar manner to that of Example 4 and the obtained reaction mixture was transferred to the next step.

Formation of tertiary amine

The above reaction mixture was heated to 50° C. and 92.5 g of epichlorohydrin (MW: 92.5) was dropped into the mixture over a period of 2 hours.

After the completion of the dropping of epichlorohydrin, the heating and stirring of the mixture were continued, while analyzing the reaction system for the residual content of N-(2-cyanoethyl)N-dodecylamine by gas chromatography every two hours. After 8 hours from the completion of the dropping of epichlorohydrin, the concentration of N-(2-cyanoethyl)-N-dodecylamine in the reaction system lowered to below 1%. Therefore the reaction mixture was transferred to the next step.

Quaternization

The above reaction mixture was cooled and fed into a 2-l autoclave together with 197 g of a 30% aqueous solution of trimethylamine (MW: 59) and 100 g of ethanol.

The obtained mixture was heated to 100° C. under stirring, aged for 6 hours and cooled.

Hydrolysis

The whole of the above reaction mixture was transferred to a 2-l four-necked flask equipped with a stirrer, a condenser, a thermometer and a dropping funnel and heated to 80° C. 40% sodium hydroxide was suitable dropped into the flask to adjust the pH of the mixture to 11. The reaction was conducted for 6 hours and discontinued.

The reaction mixture was purified by electro-dialysis. A part of the purified mixture was evaporated to dryness and subjected to IR spectroscopic analysis and mass spectrometric analysis to thereby ascertain that a compound represented by the general formula (1'), i.e., N-dodecyl-N-(3-trimethylammonio-2 hydroxypropyl)aminopropionate was formed.

Results of IR spectroscopic analysis and mass spectrometric analysis

<IR spectroscopic analysis>

An intense absorption assignable to a carboxylate ion was observed at 1560 cm$^{-1}$ (6.4 μ).

<mass spectrometric analysis>
device:
 mfd. by JEOL, Ltd., SX-102 type
 mass spectrometric type
conditions of measurement:
 introduction: direct
 ionization: FAB (Fast Atom Bombardment)
results:
 fragment
 molecular weight of ion
 373
 314
 270

Three main peaks were observed, among which the peak of 373 is assignable to a parent ion (M+1). Thus the obtained compound was ascertained to have a structure according to the present invention.

Comparative Example 1

Softazoline CH (a product of Kawaken K. K., N-cocoyl-N'-hydroxyethyl-N'-sodiumcarboxymethylethylenediamine) was used as a surfactant.

Comparative Example 2

Alanone ALE (a product of Kawaken K. K., sodium N-lauroyl-N-methyl-β-alanine) was used as a surfactant.

Comparative Example 3

Emal TD (a product of Kao Corporation, triethanolamine laurylsulfate) was used as a surfactant.

The compounds employed in Comparative Examples 1 and 2 as controls are those which have been known to be extremely lowly irritant to the skin.

(Test Example)

Test on irritativeness to skin

The irritativeness to the skin was determined by 24-hour occlusive application test on human skin.

That is, adhesive plasters for patch test each impregnated with 0.1 ml of a 0.2% (in terms of an active ingredient) aqueous solution of each of the samples were applied to 20 subjects for 24 hours. After 24 hours from the removal of the adhesive plaster, the irritativeness of the sample was evaluated. A case wherein clear erythema was caused was regarded as "positive" and the rate of the positive reaction is given in Table 1.

Foaming power

Each of the samples was diluted with 4° DH hard water so as to give a final concentration of 0.2% (in terms of an active ingredient). The obtained solution was examined for foaming power by the inversion stirring method at 40° C. with the addition of 0.3% of lanolin. The results are given by the amount (ml) of foam.

Detergency test

An artificial soil having a composition similar to that of scalp sebum (paraffin: 12%, wax ester: 21%, triglyceride: 26%, higher fatty acid: 32%, cholesterol: 5%, monoglyceride: 2%) containing 2% of carbon black was uniformly applied to a wool muslin cloth (5 cm × 5 cm) and dried. This stained cloth was placed in an about 1000-ml stainless steel cylinder containing 500 ml of a 0.6% (in terms of an active ingredient) solution of each of the samples in 4° DH water having a pH of 7.0. The resulting cylinder was shaken in a thermostatic chamber at 40° C. for 6 minutes. The resulting cloth was sufficiently rinsed with flowing water and dried. The reflectance of the cloth was determined to calculate the rate of cleansing according to the following equation:

rate of cleansing (%) =

$$\frac{\text{(reflectance after cleansing)} - \text{(reflectance before cleansing)}}{\text{(reflectance of initial cloth)} - \text{(reflectance before cleansing)}} \times 100$$

TABLE 1

| Evaluation of performances | Example | | | | Comp. Example | | |
|---|---|---|---|---|---|---|---|
| | 1 | 2 | 3 | 4 | 1 | 2 | 3 |
| irritativeness (rate of positive reaction: %) | 0 | 5 | 5 | 0 | 15 | 10 | 90 |
| foaming power (ml) | 160 | 170 | 165 | 170 | 110 | 85 | 175 |
| rate of cleansing (%) | 55 | 65 | 50 | 60 | 45 | 20 | 19 |

With respect to betaine compound (21)

EXAMPLE 21

Amination [synthesis of compound (23)]

185 g of dodecylamine (MW: 185), 200 g of ion-exchanged water and 100 g of ethanol were fed into a 2-l four-necked flask equipped with a stirrer, a condenser, a thermometer and a dropping funnel. The obtained mixture was heated to 75° C. under stirring. While keeping the mixture at that temperature, a pH electrode was inserted into the mixture and a 40% aqueous solution of sodium hydroxide was dropped into the flask to adjust the pH of the mixture to 10. 489 g of a 50% aqueous solution of 3-chloro-2-hydroxypropylenetrimethylammonium salt (MW: 188) was dropped into the flask over a period of 2 hours while keeping the pH of the mixture at 10 by the suitable dropwise addition of 40% sodium hydroxide. After the completion of the dropping of 3-chloro-2-hydroxypropylenetrimethylammonium salt, the heating and stirring of the mixture were continued with the pH thereof kept at 10, while analyzing the reaction system for dodecylamine content by high-performance liquid chromatography every hour.

After 6 hours from the completion of the dropping of 3-chloro-2-hydroxypropylenetrimethylammonium salt, the dodecylamine concentration of the reaction system lowered to 1%. Therefore the reaction mixture was transferred to the next step.

Conversion into betaine [synthesis of compound (21)]

The above reaction mixture was heated to 80° C. and 655 g of a 30% aqueous solution of sodium 3-chloro-2-hydroxypropylenesulfonate (MW: 196.5) which had been preliminarily prepared was dropped thereinto over a period of 2 hours, while keeping the pH of the mixture at 10 by the suitable dropwise addition of a 40% aqueous solution of an alkali. While keeping the pH of the reaction system at 10 and heating and stirring the system, the reaction was conducted until the concentration of the betaine precursor (23) in the system lowered to 1% as determined by high-performance liquid chromatography. Then the reaction was discontinued.

The obtained reaction mixture was purified with an electrodialyzer. A part of the purified mixture was evaporated to dryness and subjected to IR spectroscopic analysis and mass spectrometric analysis. Thus it was ascertained that a compound represented by the general formula (21), i.e., N-dodecyl-N-(3-trimethylammonio-2-hydroxypropylene)-amino-2-hydroxypropylenesulfonate (having the following structure) was formed.

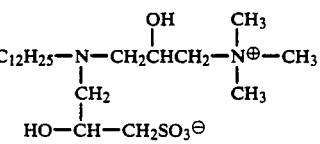

Results of IR spectroscopic analysis and mass spectrometric analysis

<IR spectroscopic analysis>

An intense absorption assignable to a sulfonate ion was observed at 1200 cm$^{-1}$ (8.33 μ).

<mass spectrometric analysis> device:
   mfd. by JEOL, Ltd., SX-102 type
   mass spectrometric type conditions of measurement:
   introduction: direct
   ionization: FAB (Fast Atom Bombardment)

results:

fragment
molecular weight of ion
439
102
58

Three main peaks were observed, among which the peak of 439 is assignable to a parent ion (M+1). Thus the obtained compound was identified as a betaine compound having the above structure.

EXAMPLE 22

The same reaction procedure as that of Example 21 was repeated except that tetradecylamine was used as the starting amine. The obtained compound was identified as a compound having a structure which will be given below by the same methods as those used in Example 21, and examined for foaming power, detergency and irritativeness to the skin. The results are given in Table 21 together with those of Example 21.

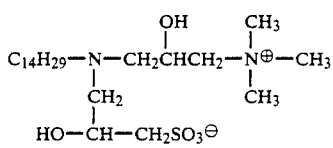

Example 23

The same reaction procedure as that of Example 21 was repeated except that 3-chloropropylenetrimethylammonium salt was used as the raw material. The obtained compound was identified as a compound having a structure which will be given below. The compound was further examined for foaming power, detergency and irritativeness to the skin. The results are given in Table 21 together with those of Example 21.

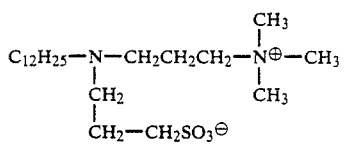

Results of IR spectroscopic analysis and mass spectrometric analysis

<IR spectroscopic analysis>

An intense absorption assignable to a sulfonate ion was observed at 1200 cm$^{-1}$ (8.33 $\mu$).

<mass spectrometric analysis>

This analysis was conducted under the same conditions as those employed in Example 21.

A parent peak of 423 (M+1) was observed, by which the obtained compound was identified as a betaine compound having the above structure.

EXAMPLE 24

The same reaction procedure as that of Example 21 was repeated except that sodium 2-bromoethanesulfonate was used as the raw material to be used in the step of conversion into betaine. The obtained compound was identified as a compound having a structure which will be given below. Further, it was examined for foaming power, detergency and irritativeness to the skin. The results are given in Table 21 together with those of Example 21.

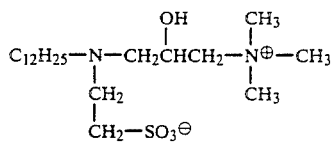

Results of IR spectroscopic analysis and mass spectrometric analysis

<IR spectroscopic analysis>

An intense absorption assignable to a sulfonate ion was observed at 1200 cm$^{-1}$ (8.33 $\mu$).

<mass spectrometric analysis>

This analysis was conducted under the same conditions as those used in Example 21.

A parent peak of 409(M+1) was observed, by which it was ascertained that the obtained compound is a betaine compound having the above structure.

EXAMPLE 25

The same reaction procedure as that of Example 21 was repeated except that oleylamine was used as the primary amine and propane sulfone was used as the raw material to be used in the step of conversion into betaine. The obtained compound had a structure which will be given below. The compound was examined for foaming power, detergency and irritativeness to the skin and the results are given in Table 21 together with those of Example 21.

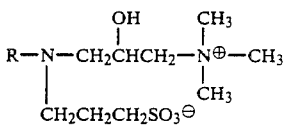

Results of IR spectroscopic analysis and mass spectrometric analysis

<IR spectroscopic analysis>

An intense absorption assignable to a sulfonate ion was observed at 1200 cm$^{-1}$ (8.33 $\mu$).

<mass spectrometric analysis>

This analysis was conducted under the same conditions as those used in Example 21.

A parent peak of 505(M+1) was observed, by which the obtained compound was identified as a betaine compound having the above structure.

(Test Example)

Test on irritativeness to skin

The irritativeness to the skin was determined by 24-hour occlusive application test on the human skin. That is, adhesive plasters for patch test each impregnated with 0.1 ml of a 0.2% (in terms of an active ingredient) aqueous solution of each of the samples were applied to 20 subjects for 24 hours. After 24 hours from the removal of the adhesive plaster, the irritativeness of the sample was evaluated. A case wherein clear erythema was caused was regarded as "positive" and the rate of positive reaction is given in Table 21.

Foaming power

Each of the samples was diluted with 40° DH hard water so as to give a final concentration of 0.2% (in terms of an active ingredient). The obtained mixture was examined for foaming power by the inversion stirring method at 40° C. with the addition of 0.3% of lanolin. The results are given by the amount (ml) of foam.

Detergency test

An artificial soil having a composition similar to that of scalp sebum (comprising 12% of paraffin, 21% of wax ester, 26% of triglyceride, 32% of higher fatty acid, 5% of cholesterol and 2% of monoglyceride) containing 2% of carbon black was uniformly applied to a wool muslin cloth (5 cm×5 cm) and dried. This stained cloth was placed in an about 1000-ml stainless steel cylinder containing 500 ml of a 0.6% (in terms of an active ingredient) solution of each of the samples in 4° DH water having a pH of 7.0. The resulting cylinder was shaken in a thermostatic chamber of 40° C. for 6 minutes. The resulting cloth was sufficiently rinsed with flowing water and dried. The reflectance of the cloth was determined to calculate the rate of cleansing according to the following equation:

$$\text{rate of cleansing (\%)} = \frac{\text{(reflectance after cleansing)} - \text{(reflectance before cleansing)}}{\text{(reflectance of initial cloth)} - \text{(reflectance before cleansing)}} \times 100$$

TABLE 21

| Evaluation of performance | Example | | | | | Control* | | |
|---|---|---|---|---|---|---|---|---|
| | 21 | 22 | 23 | 24 | 25 | 21 | 22 | 23 |
| irritativeness (rate of positive reaction: %) | 5 | 0 | 5 | 0 | 10 | 15 | 10 | 90 |
| foaming power (ml) | 155 | 165 | 160 | 170 | 140 | 110 | 85 | 175 |
| rate of cleansing (%) | 50 | 60 | 50 | 45 | 65 | 45 | 20 | 19 |

*The compounds used as controls 21 and 22 are those which have been known to be extremely mild to the skin. The compound used as control 23 is one which has been known to be excellent in foaming power.

Control 21: a product of Kawaken K. K., Softazoline CH (N-cocoyl-N'-hydroxyethyl-N'-sodiumcarboxymethylethylenediamine)

Control 22: a product of Kawaken K. K., Alanone ALE (sodium N-lauroyl-N-methyl-β-alanine)

Control 23: a product of Kao Corporation, Emal TD (triethanolamine laurylsulfate)

With respect to betaine compound (31) and detergent composition containing the same Representative examples with respect to the preparation of the betaine compound represented by the general formula (31) will now be described as Referential Examples.

Referential Example 1

185 g of dodecylamine (MW: 185), 200 g of ion-exchanged water and 100 g of ethanol were fed into a 2-l four-necked flask equipped with a stirrer, a condenser, a thermometer and a dropping funnel. The obtained mixture was heated to 75° C. under stirring.

While keeping the mixture at that temperature, a pH electrode was inserted into the mixture and a 40% aqueous solution of sodium hydroxide was dropped thereinto to adjust the pH of the mixture to 10. 489 g of a 50% aqueous solution of 3-chloro-2-hydroxypropyltrimethylammonium chloride (MW: 188) was dropped into the mixture over a period of 2 hours while keeping the pH thereof at 10 by the suitable dropwise addition of 40% sodium hydroxide.

After the completion of the dropping of 3-chloro-2-hydroxypropyltrimethylammonium chloride, the heating and stirring of the mixture was continued with the pH kept at 10 while analyzing the reaction system for dodecylamine content by high performance liquid chromatography every hour.

After 6 hours from the completion of the dropping of 3-chloro-2-hydroxypropyltrimethylammonium chloride, the concentration of dodecylamine in the reaction system lowered to 1% and therefore the reaction mixture was transferred to the next step.

The above reaction mixture was heated to 80° C. and 379 g of a 40% aqueous solution of sodium monochloroacetate (MW: 116.5) which had been preliminarily prepared was dropped thereinto over a period of 2 hours while keeping the pH of the mixture at 10 by the suitable dropwise addition of a 40% aqueous solution of an alkali. While keeping the pH of the mixture at 10 and heating and stirring the mixture, the reaction was conducted until the concentration of the precursor of the general formula (33) in the reaction system lowered to 1% as determined by high-performance liquid chromatography. Thereafter the reaction was discontinued.

The obtained reaction mixture was purified with an electrodialyzer. A part of the purified mixture was evaporated to dryness and subjected to IR spectroscopic analysis and mass spectrometric analysis. Thus it was ascertained that a compound represented by the following formula, i.e., N-dodecyl-N-(3-trimethylammonio-2-hydroxypropyl)aminoacetate was formed:

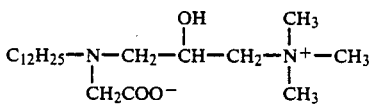

Referential Example 2

185 g of dodecylamine (MW: 185), 200 g of ion-exchanged water and 100 g of ethanol were fed into a 2-l four-necked flask equipped with a stirrer, a condenser, a thermometer and a dropping funnel. The obtained mixture was heated to 75° C. under stirring.

While keeping the mixture at that temperature, a pH electrode was inserted thereinto and a 40% aqueous solution of sodium hydroxide was dropped into the flask to adjust the pH of the mixture to 10. 489 g of a 50% aqueous solution of 3-chloro-2-hydroxypropyltrimethylammonium chloride (MW: 188) was dropped into the flask over a period of 2 hours while keeping the pH of the mixture at 10 by the suitable dropwise addition of a 40% aqueous solution of sodium hydroxide.

After the completion of the dropping of 3-chloro-2-hydroxypropyltrimethylammonium chloride, the heating and stirring of the mixture were continued with the pH thereof kept at 10 while analyzing the reaction system for dodecylamine content by high-performance liquid chromatography every hour.

After 6 hours from the completion of the dropping of 3-chloro-2-hydroxypropyltrimethylammonium chloride, the concentration of dodecylamine in the reaction system lowered to 1% and therefore the reaction mixture was transferred to the next step.

The above reaction mixture was heated to 80° C. and 655 g of a 30% aqueous solution of sodium 3-chloro-2- hydroxypropylsulfonate (MW: 196.5) which had been preliminarily prepared was dropped thereinto over a period of 2 hours while keeping the pH of the mixture at 10 by the suitable dropwise addition of a 40% aqueous solution of an alkali.

While keeping the pH of the reaction system at 10 and heating and stirring the system, the reaction was conducted until the concentration of the precursor of the general formula (33) in the system lowered to 1% as determined by high-performance liquid chromatography, and thereafter discontinued. The obtained reaction mixture was purified with an electrodialyzer. A part of the purified mixture was evaporated to dryness and subjected to IR spectroscopic analysis and mass spectrometric analysis. Thus it was ascertained that a compound represented by the following structural formula, i.e., N-dodecyl-N-(3-trimethylammonio-2-hydroxypropyl)amino-2-hydroxypropylsulfonate was formed:

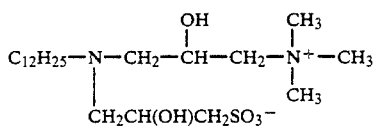

Referential Example 3 [synthesis of betaine compound (31'), route 31]

Cyanoethylation 185 g of dodecylamine and 10 g of ethanol were fed into a 2-l four-necked flask equipped with a stirrer, a condenser, a thermometer and a dropping funnel. The obtained mixture was heated to 50° C. under stirring. 53 g of acrylonitrile (MW: 53) was dropped into the mixture over a period of one hour and the obtained mixture was aged for 2 hours and analyzed for dodecylamine content by ga chromatography. The content was 0.3% and therefore the reaction mixture was transferred to the next step.

Quaternization

The above reaction mixture was heated to 80° C. and 200 g of ethanol, 50 g of ion-exchanged water and 489 g of a 50% aqueous solution of 3-chloro-2-hydroxypropyltrimethylammonium chloride (MW: 188) were dropped into the mixture over a period of 2 hours.

During the above dropping, 40% sodium hydroxide was suitably dropped into the mixture to keep the pH thereof at 9. While keeping the pH of the reaction system at 9 and heating and stirring the reaction system, the reaction was conducted until the concentration of N-(2-cyanoethyl)-N-dodecylamine in the system lowered to below 1% as determined by high-performance liquid chromatography.

Hydrolysis

In order to hydrolyze the cyano group, the temperature of the reaction mixture was lowered to 75° C. and the pH thereof was adjusted to 11 by the suitable dropwise addition of 40% sodium hydroxide. The reaction was conducted for 6 hours and thereafter discontinued.

The reaction mixture was purified by electrodialysis. A part of the purified mixture was evaporated to dryness and subjected to IR spectroscopic analysis and mass spectrometric analysis. Thus it was ascertained that a compound represented by the general formula (31'), i.e., N-dodecyl-N-(3-trimethylammonio-2-hydroxypropyl)aminopropionate was formed.

Results of IR spectroscopic analysis and mass spectrometric analysis

<IR spectroscopic analysis>

An intense absorption assignable to a carboxylate ion was observed at 1560 cm$^{-1}$ (6.4 $\mu$).

<mass spectrometric type>
device:
  mfd. by JEOL, Ltd., SX-102 type
  mass spectrometric type
conditions of measurement:
  introduction: direct
  ionization: FAB (Fast Atom Bombardment)
results:
  fragment
  molecular weight of ion
  373
  314
  270

Three main peaks were observed, among which the peak of 373 is assignable to a parent ion (M+1). Thus it was ascertained that the obtained compound has a structure according to the present invention.

Referential Example 4 [synthesis of betaine compound (31''), route 32]

Cyanoethylation

This step was conducted in a similar manner to that of Referential Example 3.

Formation of tertiary amine

The above mixture was heated to 50° C. and 92.5 g of epichlorohydrin (MW: 92.5) was dropped thereinto over a period of 2 hours.

After the completion of the dropping of epichlorohydrin, the heating and stirring of the mixture were continued while analyzing the reaction system for the residual content of N-(2-cyanoethyl)N-dodecylamine by gas chromatography every two hours. After 8 hours from the completion of the dropping of epichlorohydrin, the concentration of N-(2-cyanoethyl)-N-dodecylamine in the system lowered to below 1% and therefore the reaction mixture was transferred to the next quaternization step.

Quaternization

The above reaction mixture was cooled and fed into a 2-l autoclave together with 197 g of a 30% aqueous solution of triethylamine (MW: 59) and 100 g of ethanol.

The obtained mixture was heated to 100° C. under stirring, aged for 6 hours and cooled.

Hydrolysis

The whole of the above reaction mixture was transferred to a 2-l four-necked flask equipped with a stirrer, a condenser, a thermometer and a dropping funnel and heated to 80° C. 40% sodium hydroxide was suitably dropped into the flask to adjust the pH of the mixture to 11. The reaction was conducted for 6 hours and discontinued.

The reaction mixture was purified by electrodialysis. A part of the purified mixture was evaporated to dryness and subjected to IR spectroscopic analysis and mass spectrometric analysis. Thus it was ascertained that a compound represented by the general formula (31'), i.e., N-dodecyl-N-(3-trimethylammonio-2-hydroxypropyl)aminopropionate was formed.

Results of IR spectroscopic analysis and mass spectrometric analysis

<IR spectroscopic analysis>

An intense absorption assignable to a carboxylate ion was observed at 1560 cm$^{-1}$ (6.4 $\mu$).

<mass spectrometric analysis> device:
 mfd. by JEOL, Ltd., SX-102 type
 mass spectrometric type
conditions of measurement:
 introduction: direct
 ionization: FAB (Fast Atom Bombardment)
results:
 fragment
 molecular weight of ion
 373
 314
 270

Three main peaks were observed, among which the peak of 372 is assignable to a parent ion (M+1). Thus it was ascertained that the obtained compound has a structure according to the present invention.

EXAMPLE 31

The following betaine compounds of the present invention and comparative surfactants were examined for foaming power, stability in hard water, irritativeness to the skin and detergency according to the methods which will be described below and the results are given in Table 31:

<Surfactants used>

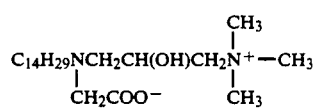

Invention 1

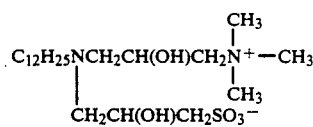

Invention 2

Comparative 1 sodium N-lauroyl-N-methyl-$\beta$-alanine
Comparative 2 triethanolamine laurylsulfate (Test methods)

Foaming power

Each of the samples was diluted with 4° DH hard water so as to give a concentration of 0.2% in terms of an active ingredient. The obtained mixture was examined for foaming power by the inversion stirring method at 40° C. with the addition of 0.3% of lanolin. The results are given in the amount (ml) of foam. Further the state of the foam was evaluated according to the following criteria:
 o: creamy
 Δ: slightly coarse
 X: coarse Stability in hard water Calcium chloride was added to a 0.1% aqueous solution of each of the samples so as to give a hardness of 100° DH. The appearance of the resulting solution was observed with the naked eye at a room temperature and evaluated.
 O: transparent solution
 X: precipitation and/or aggregation Irritativeness to skin The irritativeness to the skin was determined by 24-hour occlusive application test on the human skin. That is, adhesive plasters for patch test each impregnated with 0.1 ml of a 0.2% (in terms of an active ingredient) aqueous solution of each of the samples were applied to 20 subjects for 24 hours. After the removal of the adhesive plaster, the irritativeness of the sample was evaluated. A case wherein clear erythema was caused was regarded as "positive" and the rate of positive reaction in given in Table 31.

Detergency test

An artificial soil having a composition similar to that of scalp sebum (comprising 12% of paraffin, 12% of paraffin, 21% of wax ester, 26% of triglyceride, 32% of higher fatty acid, 5% of cholesterol and 2% of monoglyceride) containing 2% of carbon black was uniformly applied to a wool muslin cloth (5 cm×5 cm) and dried. This stained cloth was placed in an about 1000-ml stainless steel cylinder containing 500 ml of a 0.6% (in terms of an active ingredient) solution of each of the samples in 4° DH water having a pH of 7.0. The resulting cylinder was shaken in a thermostatic chamber at 40° C. for 6 minutes. The resulting cloth was sufficiently rinsed with flowing water and dried. The reflectance of the cloth was determined to calculate the rate of cleansing according to the following equation:

$$\text{rate of cleansing (\%)} = \frac{(\text{reflectance after cleansing}) - (\text{reflectance before cleansing})}{(\text{reflectance of initial cloth}) - (\text{reflectance before cleansing})} \times 100$$

TABLE 31

|  | Invention | | Comparative | |
| --- | --- | --- | --- | --- |
|  | 31 | 32 | 31 | 32 |
| irritativeness to skin | 0 | 5 | 10 | 90 |
| amount of foam (ml) | 170 | 165 | 85 | 165 |
| state of foam | O | O | Δ | Δ |
| rate of cleansing (%) | 60 | 50 | 20 | 19 |
| stability in hard water | O | O | X | X |

EXAMPLE 32

A shampoo having a formulation which will be given below was prepared.

The obtained shampoo was excellent in detergency, foaming power and stability in hard water and was extremely lowly irritant. Further, during both the shampooing and the rinsing, the hair was smooth to the touch.

<Formulation>

| | |
| --- | --- |
| C$_{14}$H$_{29}$NCH$_2$CH(OH)CH$_2$N$^+$—CH$_3$ (betaine structure with CH$_2$COO$^-$ and CH$_3$) | 15% by weight |
| betaine of laurylamidopropyl-dimethylaminoacetate | 2% by weight |
| cationized cellulose *1 | 0.2% by weight |
| polyoxyethylenesorbitan(16OEO) tristearate | 0.3% by weight |

| | |
|---|---|
| sodium benzoate | 0.3% by weight |
| dyestuff | a proper amount |
| perfume | a proper amount |
| water | the balance |
| pH: 6.5 (adjusted with citric acid) | | note)
*1: polymer JR400 (a product of UCC)

EXAMPLE 33

A body shampoo having a formulation which will be given below was prepared. The obtained body shampoo was excellent in detergency and foaming power and was lowly irritant. Further the body washed with the body shampoo was moist to the touch.

<Formulation>

| | |
|---|---|
| $\begin{array}{c} \quad\quad\quad\quad CH_3 \\ \quad\quad\quad\quad \| \\ C_{12}H_{25}NCH_2CH(OH)CH_2N^+-CH_3 \\ \quad\quad\quad\quad\quad\quad\quad\quad \| \\ \quad\quad CH_2CH(OH)CH_2SO_3^- \quad\quad CH_3 \end{array}$ | 15% by weight |
| polyoxyethylene(3) laurylglucoside | 5% by weight |

| | |
|---|---|
| (degree of polymerization of glucoside: 2.0) | |
| triethanolamine laurate | 2% by weight |
| fatty acid ester of sucrose | 1% by weight |
| glycerin | 5% by weight |
| methyl paraben | 0.3% by weight |
| ethylene glycol distearate | 2% by weight |
| dyestuff | a proper amount |
| perfume | a proper amount |
| water | the balance |
| pH: 7.5 (adjusted with citric acid) | |

What is claimed is:

1. A betaine compound represented by the general formula:

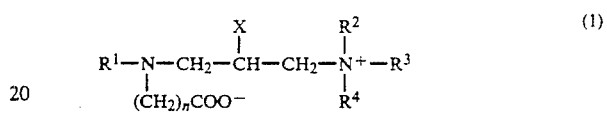

wherein $R^1$ represents a straight-chain or branched alkyl, alkenyl or hydroxyalkyl group having 8 to 22 carbon atoms; X represents H or a hydroxyl group; $R^2$, $R^3$ and $R^4$ each represent an alkyl group having 1 to 4 carbon atoms; and n represents a number of 1 to 5.

* * * * *